United States Patent [19]

Saferstein et al.

[11] 4,380,790
[45] Apr. 19, 1983

[54] MULTI-FUNCTION LIGHT DEVICE

[75] Inventors: Al Saferstein; Gilbert Spector, both of Greenwich, Conn.

[73] Assignee: Innomed Corporation, Greenwich, Conn.

[21] Appl. No.: 207,528

[22] Filed: Nov. 17, 1980

[51] Int. Cl.³ .............................................. F21V 9/00
[52] U.S. Cl. .................................. 362/231; 362/285; 362/140; 128/23; 350/256
[58] Field of Search .................. 362/19, 31, 33, 97, 362/98, 231, 330, 331, 333, 338, 268, 285, 287, 269, 275, 136, 138, 140, 804, 455, 413, 418, 419, 422, 424; 128/22, 23, 355, 395; 350/245, 246, 247, 254, 256, 253

[56] References Cited

U.S. PATENT DOCUMENTS 1,927,520  9/1933  Lafans ................................... 128/23
3,950,102  4/1976  Eiclchorst ........................... 362/231

Primary Examiner—Donald P. Walsh
Attorney, Agent, or Firm—Sprung, Horn, Kramer & Woods

[57] ABSTRACT

A multi-function light device includes a base having two opposed main surfaces and an aperture extending through the main surfaces. A first magnifying lens is mounted on the base and aligned with the aperture to enable magnified viewing through the base member from the one main surface to the other main surface. An energizable source of blacklight blue light and an energizable source of white light are mounted on the other main surface and disposed about the first magnifying lens. The light sources are connectable to an energy source. The device is particularly suitable to enable lice detection on a patient.

9 Claims, 5 Drawing Figures

FIG. 2.
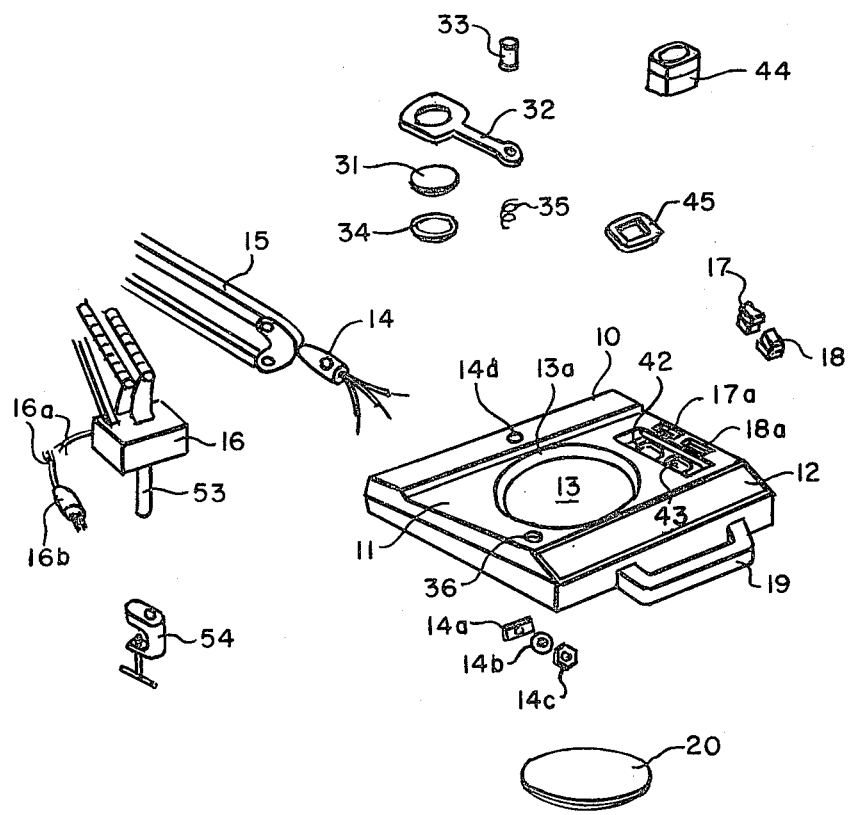
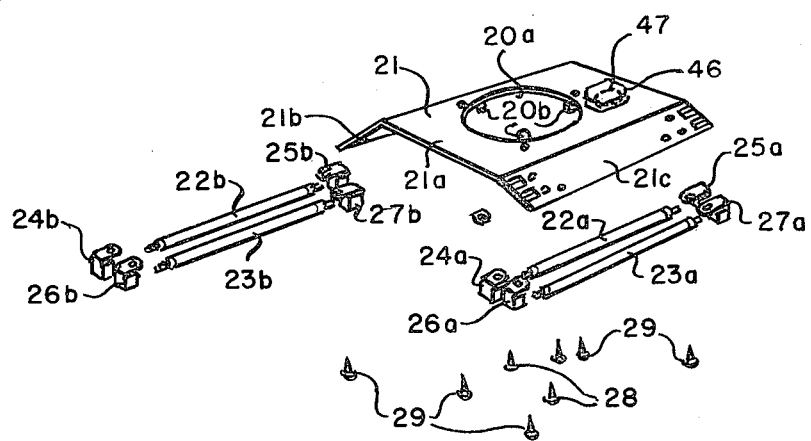

MULTI-FUNCTION LIGHT DEVICE

BACKGROUND OF THE INVENTION

The present invention relates in general to a multi-function light device and in particular to an apparatus for the detection of lice, either in the form of eggs or so-called nits or nymphal or adult lice.

Illumination devices such as medical lamps are known for use as detectors or for the sole function of illuminating an object.

In the specific area of dermatology, louse infestations have become increasingly more prevelant in the past decade throughout the United States. Past epidemics were attributed to poverty, poor sanitation and crowding due to war and economic crises. However, the recent wave of infestation in the United States has evolved in the absence of major social disturbance and has affected persons from all social economic levels, without regard for age, sex or standards of personal hygiene.

Three types of lice infest man, head lice (Pediculus humanus capitis), body lice (Pediculus humanus humanus), and pubic or crab lice (Phthirus pubic). Proper identification is very important in order to accurately facilitate treatment and preventative measures. The most commonly used method of identifying lice is through a knowledge of their preferred habitat on the infected host. Head lice are probably the most frequent variety to appear on the scalp and hair. They apparently are not apt to be found on eyebrows or eyelashes. Pubic lice most frequently infect pubic hair, however, they may also be found on coarse hair in other locations such as the exilla, eyelashes, eyebrows, mustache, or beard. Body lice spend most of their time on clothing. They seem to move to the skin to feed and are numerous where clothing is in continuous contact with the body.

Nits or louse eggs, are reportedly observed more often than nymphal or adult lice. Head lice and pubic lice attach their eggs to hairs in their respective habitats, whereas body lice attach their eggs to clothing fibers.

While treatment of lice is not complicated, proper identification is essential to recommend appropriate pediculcides or scabicides. Since the incubation of louse eggs is about one week, a patient must be treated repeatedly so as to effect a complete cure.

Conventional single function light devices or other means of detecting lice comprising magnifying glasses/loops which are used in the presence of ordinary light, have proven to be inefficient since they prove to be rather time consuming and tedious to use.

Moreover, it has been found that nits fluoresce under the influence of ultraviolet light and thus provides a means for identifying same by doctors and nurses.

SUMMARY OF THE INVENTION

The main object of the present invention is to provide a multi-function light device which has many applications, including the ability to eliminate the disadvantages of the prior art lice detectors and to provide an apparatus for the detection of lice.

These and other objects of the present invention are obtained by the multi-function light device according to the present invention which comprises a base having two opposed main surfaces and an aperture extending through the main surfaces, a first magnifying lens mounted on the base and aligned with the aperture to enable magnified viewing through the base from one main surface to the other, an energizable source of blacklight blue light and an energizable source of white light, wherein each include two bulbs mounted on the other main surface and disposed on opposite sides of the first magnifying lens and means for connecting the light sources of an energy source.

In a preferred embodiment of the present invention, a second magnifying lens is mounted on the one main surface for pivotable movement between an operative position wherein the first magnifying lens is aligned with the second magnifying lens with the second magnifying lens between the viewer and the first magnifying lens and an inoperative position out of alignment between the viewer and the first magnifying lens.

Also in the preferred embodiment, the one main surface of the base has a substantially planar portion which acts as a tray. The one main surface includes a holder for a hand-held microscope which can be used to further scrutinize a sample with the light source for the microscope being the aforementioned source of white light. Another indentation is configured to hold a sample taken from a patient.

The base is preferably mounted during use to a wall or ceiling bracket or a T-shaped stand via means which permit the positioning and maintaining of the base in any one of a plurality of desired positions. In a particularly advantageous commercial embodiment, the mounting means includes a Luxo-type arm and swivel joint which has a ballast for the two lights disposed at the end connected to the bracket or T-shape stand.

The energizable sources of light are preferably elongated lamps which are held to the underside of the base by a roof-shaped reflection which is mounted on the base to further hold the first magnifying lens in place.

The multi-function light device according to the present invention has a multitude of applications. For example, medical applications of the device include use of medical offices or dermatology, pediatrics, opthamology and general practice, hospital use, veterinary use, use in medical laboratories, for pathology, use in operating rooms, emergency rooms, intensive care rooms and in podiatry and skin care centers. The device has use for inspection purposes such as nondestructive testing, for airlines, for tooling and assembly, food inspection, stress analysis and contamination and leak protection such as the venting of fumes and the checking of printed circuits for OSHA purposes. The device has particular use for the pediculosous screening, various fungus and disease screening such as for emergency examinations for schools, institutions, camps, etc. and the checking of live stock in a similar manner. The device has industrial applications for photography and printing in the editing, layout and other phases thereof. The device can be used by museums and by geologists for the restoration of china, art and porcelain. The device can be used for hydrocarbon detection and petroleum testing, textile inspection, criminology for document examination, blood examinations and other uses. The lights that can be utilized therein are long wave ultraviolet, short wave ultraviolet, infrared, black light white light and other types of lights such as germacidal lights.

BRIEF DESCRIPTION OF THE DRAWINGS

The invention will be better understood from the following description taken in conjunction with the accompanying drawings wherein:

FIG. 2 is an exploded view of the apparatus of FIG. 1;

FIG. 4 is a side view of the base mounted on a T-stand; and

FIG. 5 is a side view of the base mounted on a wall bracket.

DETAILED DESCRIPTION OF THE PREFERRED EMBODIMENTS

Figure 1:
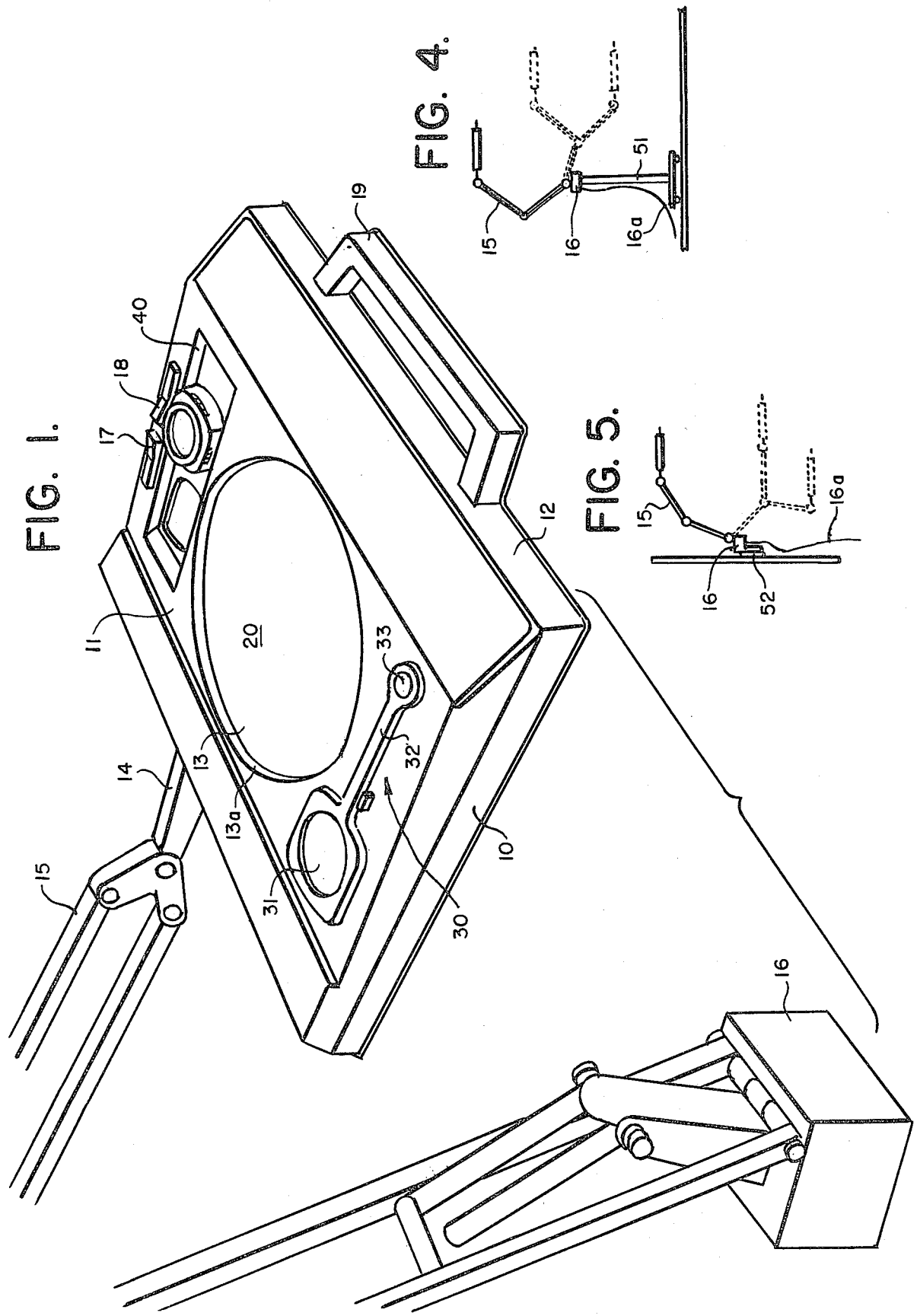
FIG. 1 is a perspective view of the apparatus according to the present invention.
Figure 3:
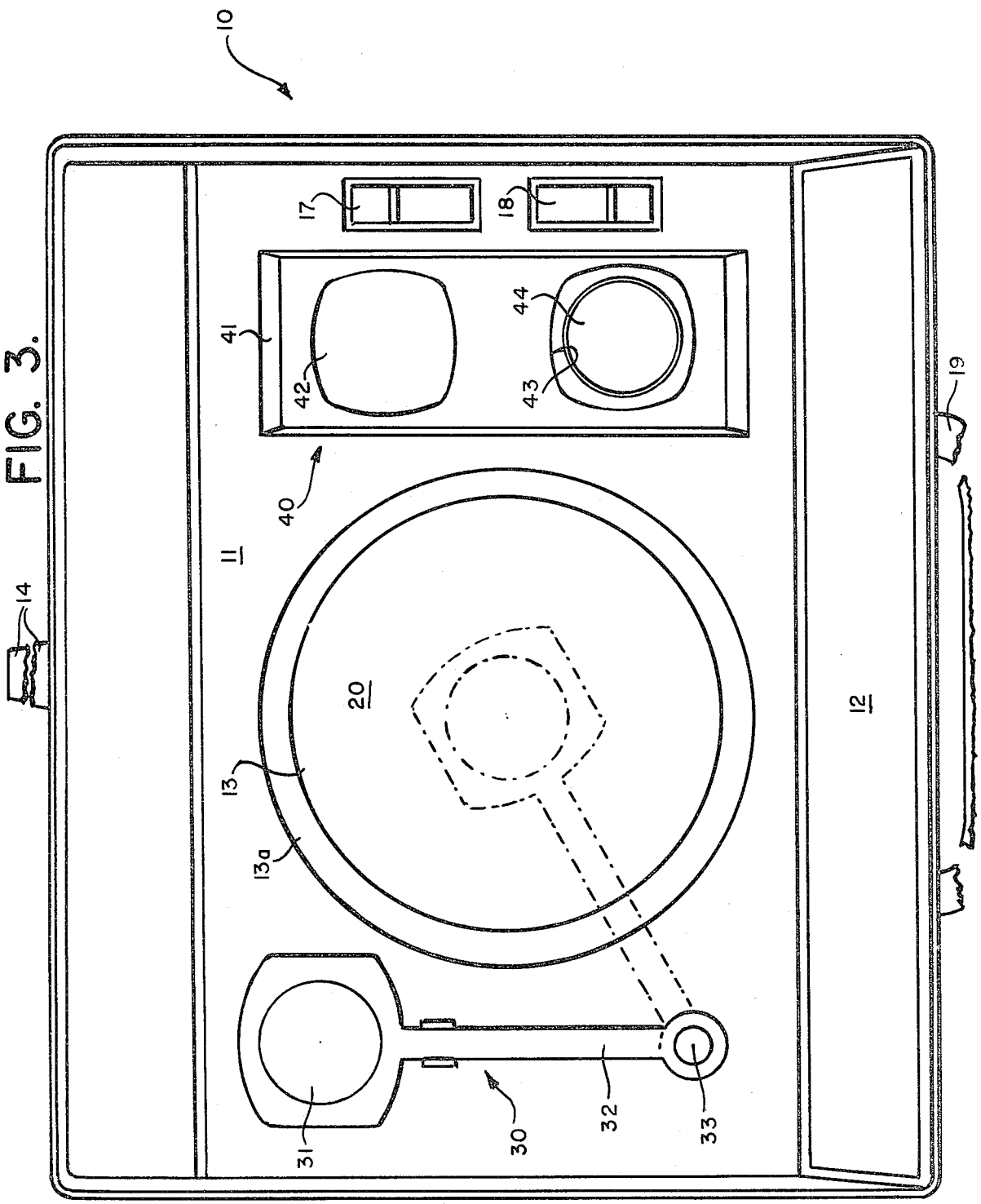
FIG. 3 is a top view showing the pivotal movement of the second magnifier.

Referring now to FIGS. 1-3, the multi-purpose light device according to the present invention includes a base 10 of rigid plastic or metal which is preferably attached via a swivel mount 14 to a movable lever assembly 15 such as preferably a Luxo-type heavy duty arm assembly which is customarily used in medical applications. At the end of the arm assembly 15 is disposed ballast means 16 which includes two ballasts, as will be explained hereinafter.

The base 10 which preferably includes means for lice detection comprises top surface 11 which is substantially planar and therefore forms a tray on which work may be performed. The base 10 also includes a bevelled side portion 12 and a handle 19 to enable one to grip the base easily and move it into position as will be described hereinafter.

The planar portion 11 includes an aperture 13 having a bevelled edge 13a and in which a magnifier lens 20, preferably of a 5" diameter and having power of 3 to 5 diopters, is mounted from the underside of the base as will be explained hereinafter. The magnifier 20 is positioned such that one can look from the top side of the base 10 through the magnifier 20 in order to view a patient thereunder as will be explained.

Also mounted on the planar surface 11 is second magnifier means 30 which includes magnifier lens 31 which is preferably 1¾" in diameter with a 10 diopter strength. Magnifier lens 31 is pivotally mounted via arm 32 and pivot pin 33 so as to be movable from the position shown in FIG. 1 to the position in dotted lines shown in FIG. 3 so as to increase the magnification of the apparatus when necessary.

As shown in FIG. 2, the apparatus according to the present invention comprises an energizable source of white light and an energizable source of black light blue light comprising lamps 23a, 23b, 22a, 22b respectively. These lamps, are mounted on either side of the magnifier 20 on the underside of the base 10 in a manner which will be set forth hereinafter. The black light blue lamps are preferably General Electric F6TBLB and the white light lamps are preferably General Electric F6T5CW.

The lamps 22a, 22b, and 23a, 23b are energized by the circuit including power line cord 16a having a plug 16b at the end thereof which feeds AC voltage to the double ballast means 16 including a conventional double ballast, the output of which is fed via wires in the arm assembly 15 and the swivel connector 14 to switches 17 and 18 which are mounted in aperture 17a, 18a in the planar portion 11 of the base 10.

Switch 17 is placed in series with the power to the white light lamps 23a, 23b and switch 18 is placed in series with the power to black light blue lamps 22a, 22b. In use, both switches 17 and 18 are simultaneously actuated such that both sets of lamps are energized. Upon the total illumination from both the white light lamps and the black light blue lamps, the user can then decide whether to use either the black light blue light alone or the white light alone by deenergizing the unneeded lamps.

The black light blue lamps provide the black light blue for fluorescing and thus enable detection of any lice in the hair of patient. Thus upon initial use, after both sets of lamps have been energized, switch 17 is placed in the off position thus leaving only the black light blue lamps in the energized condition.

If on the other hand the fluorescing of the light is not desired, but rather one utilizing the apparatus wants to observe a portion of the body of a patient under high intensity ambient light, switch 18 is placed in the off state thus turning off the black light blue lamp and leaving only the white light lamps in the energized condition.

Also positioned in the planar portion 11 of the base 10 is a sample station 40 for the analysis of samples taken from a patient. The sample station 40 includes a rectangular shaped well 41 having two circular depressions 42, 43 therein. In depression 42, can be situated a disposable plastic dish 45 (see FIG. 2) which serves as a sample holder. Depression 43 is bottomless and is aligned with aperture 46 in reflector 21. A hand-held microscope 44 having a translucent lower portion in held in place in holder 47 so that the white and black lights can provide illumination therefor. One takes a sample from dish 45 and places it in the microscope 44 which is then set in place to permit close inspection of the sample taken from a patient.

Referring again to FIG. 2, the means for mounting the magnifier 20 to the underside of the base 10 includes a roof shaped reflector 21 including shaped sides 21b and 21c and a planar intermediate section 21a having a central aperture 20a configured to be smaller than the diameter of the magnifier 20 and retaining tabs 20b for fixing the magnifier 20 in place. The reflector 21 is held to the base portion by via screws 29. The lamps 22a, 22b and 23a, 23b are mounted on the underside of the reflector on the sloped portions thereof 21b, 21c via conventional fluorescent light brackets 24a-27a and 24b-27b (not shown). The brackets are held on the underside of the reflector via screws 28.

The secondary magnifier 30 is shown in more detail in FIG. 2 and comprises the arm 32 in which lens 31 is seated by a retaining ring 34. The pivotal mounting of arm 32 is carried out by a snap-in retainer stud 33 and spring 35 which is received in aperture 36 of planar portion 11.

The swivel mounting of the arm 15 is carried via aperture 14d in the side wall of base 10 and with washer 14a, locking washer 14b and nut 14c.

The ballast means 16 conveniently includes a mounting rod 53 which is received in clamp 54 and thus enables the apparatus to be mounted onto a table or the like.

Alternatively, as shown in FIGS. 4 and 5, ballast 16 can be connected to a T-stand 51 to provide portable use of the apparatus, or to a wall or ceiling bracket 52 so that the apparatus can be permanently installed in place.

It will be appreciated that the instant specification and claims are set forth by way of illustration and not limitation, and that various modifications and changes may be made without departing from the spirit and scope of the present invention.

We claim:

1. A multi-function light device comprising: a base having two opposed main surfaces and an aperture extending through the main surfaces; a first magnifying lens mounted on the base and aligned with the aperture to enable magnified viewing through the base from one main surface to the other main surface; an energizable source of blacklight blue light and an energizable source of white light; means mounting the light sources on the other main surface about the first magnifying lens; and means for connecting the light sources to an energy source wherein the one main surface of the base has a substantially planar portion forming the top thereof and at least one indentation for receiving an object.

2. The device according to claim 1, further comprising a second magnifying lens mounted on the one main surface for pivotable movement between an operative position wherein the first magnifying lens is aligned with the second magnifying between same and the viewer and a position out of alignment between the first magnifying lens and the viewer.

3. The device according to claim 2, wherein the connecting means comprises two power switches for the two light sources and power leads connected thereto for connection to an ac outlet.

4. The device according to claim 3, further comprising an aperture in the base for permitting light to pass towards the one main surface, a handheld microscope disposable in the aperture for illumination by the source of white and black light and wherein the indentation is configured to receive a sample for scrutinizing with the microscope.

5. The device according to claim 4, further comprising a wall bracket and means connecting the base to the bracket to permit the positioning and maintaining of the base in any one of a plurality of desired positions during use.

6. The device according to claim 4, further comprising a T-shaped stand and means connecting the base to the stand to permit the positioning and maintaining of the base in any one of a plurality of desired positions during use.

7. The device according to claim 5 or claim 6, wherein the energy source connecting means comprises ballast means for the lights disposed at the end of the base connecting means opposite the base.

8. The device according to claim 1, wherein the means mounting the light sources comprises a roof shaped reflector connected to the other main surface.

9. A lice detector comprising a device according to claim 4.

* * * * *